United States Patent [19]

Saito et al.

[11] 4,122,174
[45] Oct. 24, 1978

[54] COMBATING PESTS WITH O-ALKYL-N-SULFAMYL-PHOSPHORAMIDOTHIOLATES

[75] Inventors: Junichi Saito; Akio Kudamatsu; Kozo Shiokawa; Yoshio Kurahashi; Shinichi Tsuboi, all of Tokyo, Japan

[73] Assignee: Nihon Tokushu Noyaku Seizo K.K., Tokyo, Japan

[21] Appl. No.: 833,924

[22] Filed: Sep. 16, 1977

[30] Foreign Application Priority Data

Sep. 20, 1976 [JP] Japan .................................. 51-111745

[51] Int. Cl.$^2$ .......................... A01N 9/36; C07F 9/24
[52] U.S. Cl. ..................................... 424/211; 260/944
[58] Field of Search ................. 260/944, 938; 424/211

[56] References Cited

PUBLICATIONS

Nagasawa et al, "Chemical Abstracts", vol. 60, 4014, Abstract of Japanese Patent 6199(63).

*Primary Examiner*—Anton H. Sutto

*Attorney, Agent, or Firm*—Burgess, Dinklage & Sprung

[57] ABSTRACT

O-Alkyl-N-sulfamyl-phosphoramidothiolates of the formula

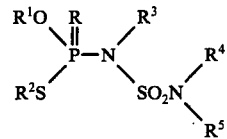

in which
   $R^1$ is alkyl with 1-6 carbon atoms,
   $R^2$ is alkyl or alkenyl with up to 6 carbon atoms,
   $R^3$ is alkyl with 1-6 carbon atoms or aryl,
   $R^4$ is alkyl with 1-6 carbon atoms,
   $R^5$ is alkyl with 1-6 carbon atoms or aryl, and
   X is oxygen or sulfur,
which possess insecticidal, acaricidal, nematicidal and fungicidal properties.

11 Claims, No Drawings

COMBATING PESTS WITH O-ALKYL-N-SULFAMYL-PHOSPHORAMIDOTHIOLATES

The present invention relates to and has for its objects the provision of particular new O-alkyl-N-sulfamyl-phosphoramidothiolates which possess insecticidal, acaricidal, nematicidal and fungicidal properties, active compositions in the form of mixtures of such compounds with solid and liquid dispersible carrier vehicles, and methods for producing such compounds and for using such compounds in a new way especially for combating pests, e.g. insects, acarids, nematodes and fungi, with other and further objects becoming apparent from a study of the within specification and accompanying examples.

Japanese Patent Publication No. 6199/63 discloses that organophosphorus compounds of the general formula $$\begin{array}{c} RO \\ \diagdown \\ RO \end{array} \overset{X}{\underset{\|}{P}} - NH - \overset{O}{\underset{\|}{S}} - N \begin{array}{c} R' \\ \diagup \\ R'' \end{array} \quad (X)$$

wherein

R stands for lower alkyl,

R' and R", which may be the same or different, each stand for hydrogen or lower alkyl, and X stands for an oxygen atom or a sulfur atom, have an insecticidal activity.

Hitherto, Parathion has been widely used as an insecticide, for example for controlling rice borers, planthoppers and leafhoppers which are important insects that are harmful to rice. The use of Parathion, however, has been suspended in some areas, particularly in Japan, because despite its excellent effectiveness against the pests, there is considered to be a great danger of its causing acute toxicity to mammals.

Furthermore the long-term use of large amounts of organophosphorus compounds, such as Parathion, EPN, BAYCID and Sumithion, organochlorine compounds, such as BHC and DDT, and carbamate compounds, such as Sevin, has resulted in the pests attaining resistance to these chemicals.

Hence there is a need for new pesticides which have only a low toxicity to warm-blooded animals but which are effective against those pests that have attained resistance to prior-art pesticides.

The present invention now provides, as new compounds, the phosphoric acid amide esters of the general formula $$\begin{array}{c} R^1O \\ \diagdown \\ R^2S \end{array} \overset{X}{\underset{\|}{P}} - N \begin{array}{c} R^3 \\ \diagdown \\ SO_2N \end{array} \begin{array}{c} R^4 \\ \diagdown \\ R^5 \end{array} \quad (I)$$

in which $R^1$ represents alkyl with 1–6 carbon atoms, $R^2$ represents alkyl or alkenyl with up to 6 carbon atoms, $R^3$ represents alkyl with 1–6 carbon atoms or aryl, $R^4$ represents alkyl with 1–6 carbon atoms, $R^5$ represents alkyl with 1–6 carbon atoms or aryl, and X represents oxygen or sulfur.

It has been found that compounds of the formula (I) exhibit unusually strong insecticidal, acaricidal, nematicidal and fungicidal activities, and possess a higher effectiveness and a wider controlling effect than compounds of the formula (X); particularly, they have an excellent activity against spider mites that have attained resistance to various known organophosphorus pesticides.

Preferably, in formula (I), $R^1$ represents alkyl with 1–4 carbon atoms (namely, methyl, ethyl, n- or isopropyl or n-, sec.-, tert.- or isobutyl), $R^2$ represents alkyl with 1–4 carbon atoms or alkenyl with 2–4 carbon atoms (for example vinyl, allyl or butenyl), $R^3$ represents alkyl with 1–4 carbon atoms or phenyl, $R^4$ represents alkyl with 1–4 carbon atoms and $R^5$ represents alkyl with 1–4 carbon atoms or phenyl. In a preferred sub-group $R^1$ is ethyl and $R^2$ is n-propyl, or is ethyl, n-butyl, sec.-butyl or allyl.

The present invention also provides a process for the preparation of a compound of the formula (I), in which (a) a (di)thiophosphoryl halide of the general formula $$\begin{array}{c} R^1O \\ \diagdown \\ R^2S \end{array} \overset{X}{\underset{\|}{P}} - Hal \quad (II),$$

in which $R^1$, $R^2$ and X have the meanings stated above and

Hal represents halogen, preferably chlorine, is reacted with a sulfamide salt of the general formula $$\begin{array}{c} R^4 \\ \diagdown \\ R^5 \end{array} NSO_2N \begin{array}{c} R^3 \\ \diagdown \\ M^1 \end{array} \quad (III),$$

in which $R^3$, $R^4$ and $R^5$ have the meanings stated above, and $M^1$ represents an alkali metal, preferably sodium or potassium, or (b), provided that X is to represent oxygen, a phosphoramidothioate salt of the general formula $$\left[ \begin{array}{c} R^4 \\ \diagdown \\ R^5 \end{array} NSO_2 - N \begin{array}{c} R^3 \\ | \\ \end{array} \begin{array}{c} OR^1 \\ | \\ P - O \\ | \\ S \end{array} \right] M^2 \quad (IV),$$

in which $R^1$, $R^3$, $R^4$ and $R^5$ have the meanings stated above, and $M^2$ represents an alkali metal (preferably sodium or potassium) or an ammonium group, is reacted with an alkylating or alkenylating agent of the general $$R^2Y \quad (V),$$

in which $R^2$ has the meaning stated above,

Y represents halogen or a sulfonic acid group (for example a benzenesulfonate, p-toluenesulfonate or monopropylsulfate group).

The phosphoramidothioate salt (IV) to be used in process variant (b) can be prepared by reacting a phosphoramidothioate of the general formula

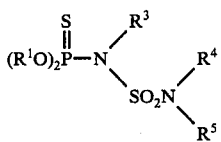 (VI), in which
R¹, R³, R⁴ and R⁵ have the meanings stated above, with a dealkylating agent of the general formula $$ZSM^2 \qquad (VII),$$

in which M² has the meaning given above, and
Z is hydrogen, alkyl (preferably with 1-4 carbon atoms) or alkoxythiocarbonyl (for example methoxythiocarbonyl or ethoxythiocarbonyl).

Specific examples of the (di)thiophosphoryl halides of the general formula (II) are: O-ethyl-S-ethylthiophosphoryl chloride, O-ethyl-S-n-propylthiophosphoryl chloride, O-ethyl-S-n-butylthiophosphoryl chloride, O-ethyl-S-allylthiophosphoryl chloride, and O-ethyl-S-n-propyldithiophosphoryl chloride.

Examples of the sulfamide salts of the general formula (III) are: sodium N,N-dimethyl N'-methylsulfamide, sodium N,N-diethyl N'-methylsulfamide, sodium N,N-dimethyl- N'-isopropylsulfamide, sodium N-methyl N-phenyl N'-methylsulfamide and sodium N,N-dimethyl N'-phenylsulfamide, and the corresponding potassium salts.

Process variant (a) can be illustrated by the following equations:

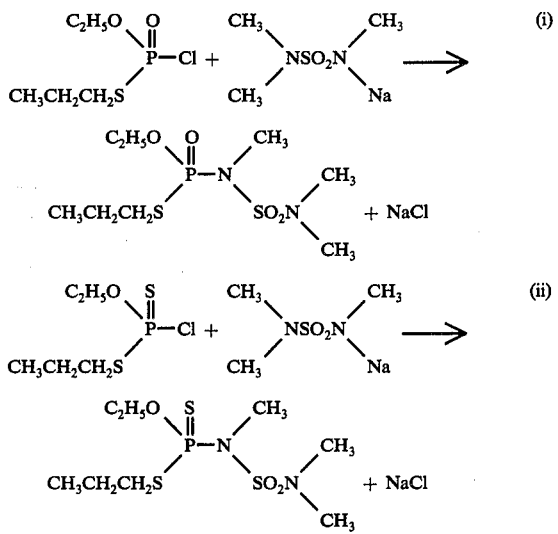

Process variant (a) of the present invention is carried out preferably using a solvent or diluent. Examples of such solvents or diluents are water and inert organic solvents selected from aliphatic, alicyclic and aromatic hydrocarbons, which optionally may be chlorinated, such as hexane, cyclohexane, petroleum ether, ligroin, benzene, toluene, xylene, methylene chloride, chloroform, carbon tetrachloride, ethylene chloride, trichloroethylene and chlorobenzene; ethers, such as diethyl ether, methyl ethyl ether, diisopropyl ether, dibutyl ether, propylene oxide, dioxane and tetrahydrofuran; ketones, such as acetone, methyl ethyl ketone, methyl isopropyl ketone and methyl isobutyl ketone; nitriles, such as acetonitrile, propionitrile and acrylonitrile; alcohols, such as methanol, ethanol, isopropanol, tert.-butanol and ethylene glycol; esters, such as ethyl acetate and amyl acetate; acid amides, and sulfoxides, such as dimethyl sulfoxide and dimethyl sulfone; and bases, such as pyridine.

Process variant (a) of the present invention can be performed in a wide temperature range. In general, the process is carried out at a temperature between −20° C and the boiling point of the mixture, preferably at a temperature of from 0° to 100° C. Furthermore, the reaction is carried out preferably at atmospheric pressure, although it can also be performed under an elevated or reduced pressure.

Specific examples of the phosphoramidothioate salts of the general formula (IV) are: potassium O-ethyl-N-methyl-N-(dimethylsulfamyl)-phosphoramidothioate, potassium O-ethyl-N-methyl-N-(diethylsulfamyl)-phosphoramidothioate, potassium O-ethyl-N-isopropyl-N-(dimethylsulfamyl)-phosphoramidothioate, potassium O-ethyl-N-methyl-N-(N'-methyl-N'-phenylsulfamyl)-phosphoramidothioate and potassium O-ethyl-N-phenyl-N-(dimethylsulfamyl)-phosphoramidothioate, as well as the corresponding sodium salts, triethylammonium salts, dimethylanilinium salts and pyridinium salts.

Examples of the alkylating and alkenylating agents of the general formula (V) are: ethyl, n-propyl, n-butyl or allyl chloride, ethyl, n-propyl, n-butyl or allyl bromide, ethyl, n-propyl, n-butyl or allyl benzenesulfonate, ethyl, n-propyl, n-butyl or allyl p-toluenesulfonate, diethyl, di-n-propyl, di-n-butyl or di-allyl sulfate, and monoethyl, n-propyl, n-butyl or allyl sulfate.

Examples of the phosphoramidothioates of the general formula (VI) are: D,D-diethyl-N-methyl-N-)dimethylsulfamyl) phosphoramidothioate, O,O-diethyl-N-methyl-N-(diethylsulfamyl) phosphoramidothiate, O,O-diethyl-N-isopropyl-N-(dimethylsulfamyl) phosphoramidothioate, O,O-diethyl-N-methyl-N-(N'-methyl-N'-phenylsulfamyl) phosphoramidothioate, and O,O-diethyl-N-phenyl-N-(dimethylsulfamyl) phosphoramidothioate.

Examples of the dealkylating agents of the general formula (VII) are: sodium hydrosulfide, potassium hydrosulfide. sodium methanethiolate, potassium ethanethiolate, sodium 2-propanethiolate, potassium methylxanthogenate, potassium ethylxanthogenate, and ammonium sulfide.

Process variant (b) of the present invention can be illustrated by the following equations.

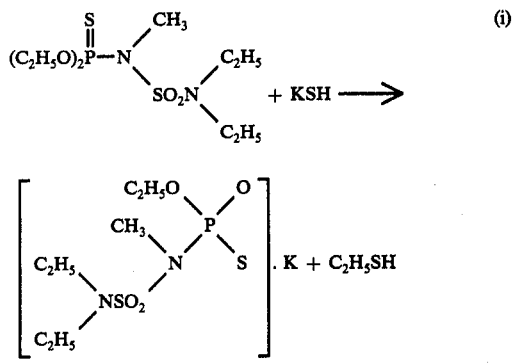

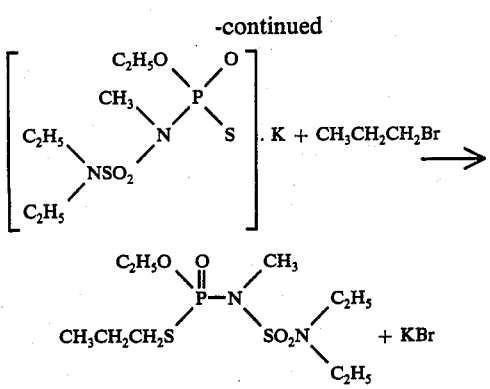

In the above sequence, the potassium O-ethyl-N-methyl-N-(diethylsulfamyl)-phosphoramidothioate, which is obtained in the first step, can be isolated. However, it is also possible to react it in situ, that is without isolation, with the alkylating agent to obtain O-ethyl-S-n-propyl-N-methyl-N-(diethylsulfamyl)-phosphoramidothiolate having a high purity and in a high yield.

In carrying out process variant (b) an inert solvent or diluent is preferably used. The solvents mentioned above in connection with process variant (a) may be used to obtain the desired product in a high purity and in a high yield.

A wide range of temperature can be employed in process variant (b). Generally, the reaction is effected at a temperature between −20° C and the boiling point of the mixture, preferably at from 0° to 100° C. Although it is desirable for the reaction to be carried out at atmospheric pressure, it is also possible to perform the reaction under an elevated or reduced pressure.

As already mentioned, the compounds according to the present invention are distinguished by an excellent insecticidal, acaricidal and nematicidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine, since they are also active against animal parasites, in particular ectoparasites such as parasitic fly larvae, spiders, ticks and nematodes.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa, spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedium, Piesma quadrata, Cimex lectularis, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria, spp., *Oryzaephilus surinamensis,* Anthonomus spp., Sitophilus spp., *Otiorrhynchus sulcatus, Cosmopolites sordidus, Ceuthorrhynchus assimilis, Hyper postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example Acarus siro, Argas spp., Ornithodoros spp., *Dermanyssus gallinae, Eriophyes ribis, Phyllocoptruta oleivora, Boophilus spp.*, Rhipicephalus spp., Amblyomma spp., Hyalomma spp., Ixodes spp., Psoroptes spp., Chorioptes spp., Sarcoptes spp, Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

The active compounds according to the invention also exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The compounds of the present invention exhibit an excellent effect particularly against *Piricularia oryzae* and *Pellicularia sasaki,* which cause important diseases of rice plants, showing both a persistent preventive effect and a curative effect. Accordingly, the compounds can control these pathogenic fungi at the same time.

Owing to their superior osmotic action, the compounds of the present invention exert an excellent fungicidal activity and reproduction-inhibiting activity against phytopathogenic fungi that are parasitic on the paddy rice plant and can therefore be applied for their control.

The compounds of the present invention can be quite conveniently used as water surface-applicable agents against diseases of plants caused by pathogenic fungi, and in view of their additional insecticidal, acaricidal and nematocidal activities, they can save labor in agricultural production.

In addition, the compounds of the invention, which do not contain such poisonous heavy metals as mercury and arsenic, cause no anxiety about the residual toxicity of the harvest. Moreover, their toxicity towards fish is low.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Purssian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides, acaricides, nematicides and fungicides, or bactericides, rodenticides, herbicides, fertilizers, growth-regulating agents, bird repellents, plant nutrients, agents for improving soil structure, etc., if desired, or in the form or particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–20, preferably 0.005–10%, by weight of the mixture. Thus, the present invention contemplates overall composition which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound. It is also possible to spread the active compound preparation or the active compound itself on plants or parts of plants or to inject the active compound preparation or the active compound itself into the soil. It is also possible to treat the seeds of plants.

In general, 0.03 to 10 kg, preferably 0.3 to 6 kg, of active compound are employed per hectare of soil surface. However, it is possible to use higher or lower amounts and in certain circumstances this may prove necessary.

Furthermore, the present invention contemplates methods of selectively killing, combating or controlling pests, e.g. insects, acarids, nematodes and fungi, which comprises applying to at least one of correspondingly (a) such insects, (b) such acarids, (c) such nematodes, (d) such fungi, and (e) the corresponding habitat thereof, i.e. the locus to be protected, e.g. to a growing crop, to an area where a crop is to be grown or to a domestic animal, a correspondingly combative or toxic amount, i.e. an insecticidally, acaricidally, nematicidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

Processes for preparing the particular new compounds of the present invention are illustrated, without limitation, by the following examples:

EXAMPLE 1

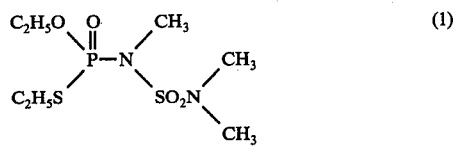

(1)

17.6 grams of sodium N,N-dimethyl-N'-methylsulfamide were suspended in 150 ml of toluene, and 18.9 grams of O-ethyl-S-ethylphosphoryl chloride were added. The mixture was then heated at 70° to 80° C for 3 to 5 hours to complete the reaction. After completing the reaction, the reaction mixture was cooled down to room temperature, washed with water and a 1% aqueous sodium hydroxide solution and dried over anhydrous sodium sulfate.

Evaporation of the toluene under reduced pressure afforded 22 grams, as a colorless oil, of O-ethyl-S-ethyl-N-methyl-N-(dimethylsulfamyl) phosphoramidothiolate ($n_D^{20}$ = 1.4886).

EXAMPLE 2

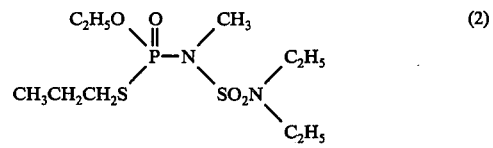

(2)

5.6 grams of potassium hydroxide were dissolved in 100 ml of ethanol and saturated with hydrogen sulfide gas at room temperature to prepare an ethanol solution of potassium hydrosulfide.

To the resulting solution were added 32 grams of O,O-diethyl-N-methyl-N-(diethylsulfamyl) phosphoramidothiolate, and the mixture was stirred at 70° to 75° C for 4 to 5 hours. After the internal temperature had been lowered to about 40° C, 14 grams of n-propyl bromide were added to the product. The mixture was further stirred for 3 hours at 65° to 70° C in order to complete the reaction. The volatile component was evaporated from the reaction mixture under reduced pressure. Toluene was added to the residue and the mixture was washed with water and a 1% aqueous sodium hydroxide solution. After drying over anhydrous sodium sulfate, the toluene was evaporated off to yield 20 grams, as a colorless oil, of O-ethyl-S-N-propyl-N-methyl-N-(diethylsulfamyl) phosphoramidothiolate ($n_D^{20}$ = 1.4805).

EXAMPLE 3

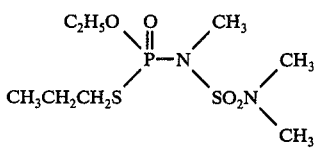

(3)

30 grams of potassium O-ethyl-N-methyl-N-(dimethylsulfamyl) phosphoramidothioate were dissolved in 150 ml of methyl ethyl ketone and the solution was mixed with 14 grams of n-propyl bromide. The mixture was heated for 3 hours at 60° to 70° C in order to complete the reaction. After distilling off the methyl ethyl ketone, toluene was added to the residue, followed by washing with water and a 1% aqueous sodium hydroxide solution. After drying over anhydrous sodium sulfate, the toluene was evaporated off under reduced pressure to afford 23 grams, as a colorless oil, of O-ethyl-S-n-propyl-N-methyl-N-(dimethylsulfamyl) phosphoramidothiolate ($n_D^{20}$ = 1.4865).

The following compounds were prepared by methods analogous to those of the preceding examples:

Table 1

$$\underset{R^2S}{\overset{CH_3O}{\diagdown}}\overset{O}{\underset{\parallel}{P}}-N\underset{SO_2N\diagdown R^5}{\overset{R^3}{\diagup}\diagup CH_3}$$ (VIII)

| Compound No. | $R^2$ | $R^3$ | $R^5$ | Refractive index $n_D^{20}$ |
|---|---|---|---|---|
| 4 | n-C$_4$H$_9$ | CH$_3$ | CH$_3$ | 1.4843 |
| 5 | CH$_2$=CHCH$_2$ | CH$_3$ | CH$_3$ | 1.5001 |
| 6 | n-C$_3$H$_7$ | i-C$_3$H$_7$ | CH$_3$ | 1.4786 |
| 7 | n-C$_3$H$_7$ | CH$_3$ | Phenyl | 1.5256 |
| 8 | n-C$_3$H$_7$ | Phenyl | CH$_3$ | 1.5127 |

EXAMPLE 4

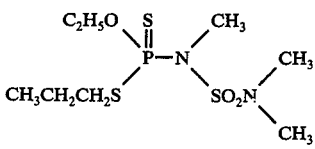

(9)

17.6 grams of sodium N,N-dimethyl-N'-methylsulfamide were suspended in 100 ml of acetonitrile. To the suspension were added 21.9 grams of O-ethyl-S-propyl-dithiophosphoryl chloride. The mixture was gradually heated and stirred for 4 to 5 hours at 35° to 45° C. After completion of the reaction, the acetonitrile was evaporated off. To the residue after distillation was added toluene, and the mixture was washed with water and 1% aqueous sodium hydroxide solution. After drying the toluene layer over anhydrous sodium sulfate, the toluene was evaporated off under reduced pressure, and the residue was dried for 1 hour at 70° C/1 mm Hg. 21 grams of O-ethyl-S-n-propyl-N-methyl-N-(dimethylsulfamyl) phosphoramidodithioate were obtained as a colorless oil ($n_D^{20}$ = 1.5155).

The following compounds were prepared by methods analogous to those described above:

Table 2

$$\underset{n-C_3H_7S}{\overset{C_2H_5O}{\diagdown}}\overset{S}{\underset{\parallel}{P}}-N\underset{SO_2N\diagdown R^5}{\overset{R^3}{\diagup}\diagup R^4}$$ (IX)

| Compound No. | $R^3$ | $R^4$ | $R^5$ | Refractive index ($n_D^{20}$) |
|---|---|---|---|---|
| 10 | CH$_3$ | C$_2$H$_5$ | C$_2$H$_5$ | 1.5105 |
| 11 | Phenyl | CH$_3$ | CH$_3$ | 1.5360 |

Other compounds which can be similarly prepared include:

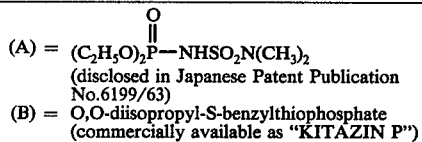

| Compound No. | $R^1$ | $R^2$ | $R^3$ | $R^4$ | $R^5$ | X |
|---|---|---|---|---|---|---|
| 12 | n-C$_4$H$_9$ | CH$_3$ | CH$_3$ | CH$_3$ | CH$_3$ | O |
| 13 | C$_2$H$_5$ | CH$_3$<br>\|<br>—CHCH=CH$_2$ | CH$_3$ | CH$_3$ | CH$_3$ | S |
| 14 | C$_2$H$_5$ | n-C$_3$H$_7$ | CH$_3$ | i-C$_3$H$_7$ | CH$_3$ | S |
| 15 | C$_2$H$_5$ | n-C$_3$H$_7$ | CH$_3$ | CH$_3$ | n-C$_4$H$_9$ | O |

The superior activities of the novel compounds can be seen in the following comparative examples wehrein the compounds according to the present invention are each identified by the number (given in brackets, from the foregoing preparative examples.

While the known comparison compounds are identified as follows:

(A) = $(C_2H_5O)_2\overset{O}{\underset{\parallel}{P}}-NHSO_2N(CH_3)_2$
 (disclosed in Japanese Patent Publication No.6199/63)
(B) = O,O-diisopropyl-S-benzylthiophosphate (commercially available as "KITAZIN P")

EXAMPLE 5

Test on larvae of Prodenia litura
Solvent: xylene, 3 parts by weight
Emulsifier: polyoxyethylene alkylphenyl ether, 1 part by weight To form a suitable preparation of the active compound, 1 part by weight of the active compound was mixed with the above amount of the solvent containing the above amount of the emulsifier, and the mixture was diluted with water to a predetermined concentration.

Sweet-potato leaves were dipped in an aqueous preparation, of a predetermined concentration, of the active compound. After drying in the air, the leaves were placed in a Petri dish 9 cm in diameter. Then, 10 third instar larvae of *Prodenia litura Fabricius* were placed in the Petri dish. The dish was placed in a constant-temperature room at 28° C. Twenty-four hours later, the number of dead larvae was determined in order to calculate the kill ratio. The results are shown in Table 3.

Table 3

| Compound No. | Kill ratio (%) at a concentration of active compound (ppm) of | | | |
|---|---|---|---|---|
| | 1000 | 300 | 100 | 50 |
| (1) | 100 | 100 | | |
| (2) | 100 | 100 | 100 | 100 |
| (3) | 100 | 100 | 100 | 100 |
| (4) | 100 | | | |
| (5) | 100 | | | |

Table 3-continued

| Compound No. | Kill ratio (%) at a concentration of active compound (ppm) of | | | |
|---|---|---|---|---|
| | 1000 | 300 | 100 | 50 |
| (6) | 100 | 100 | | |
| (7) | 100 | 100 | | |
| (8) | 100 | 100 | 100 | |
| (9) | 100 | 100 | | |
| (10) | 100 | | | |
| (11) | 100 | | | |
| (A) | 0 | 0 | 0 | 0 |

EXAMPLE 6

Test on Callosobruchus chinensis

The bottom of a Petri dish 9 cm in diameter was covered with a filter paper, onto which was placed 1 ml of an aqueous preparation, at a predetermined concentration, of the active compound (prepared as in Example 5). 20 Callosobruchus chinensis beetles were placed therein, and the Petri dish was allowed to stand in a constant-temperature room at 28° C. for 24 hours. After 24 hours had elapsed, the number of dead beetles was determined in order to calculate the kill ratio. The results are shown in Table 4.

Table 4

| Compound No. | Kill ratio (%) at a Concentration of active ingredient (ppm) of | | |
|---|---|---|---|
| | 1000 | 100 | 10 |
| (1) | 100 | | |
| (2) | 100 | 100 | |
| (3) | 100 | | |
| (4) | 100 | | |
| (5) | 100 | | |
| (6) | 100 | | |
| (7) | 100 | 100 | |
| (8) | 100 | 100 | 100 |
| (9) | 100 | 100 | |
| (10) | 100 | 100 | 100 |
| (11) | 100 | 100 | 100 |
| (A) | 0 | 0 | 0 |

EXAMPLE 7

Test on the mite Tetranychus cinnabarinus (spray test)

The leaves of kidney bean plants in the two-leaf stage were infested with 50 to 60 larvae of Tetranychus cinnabarinus. The kidney bean plants were cultivated in pots each 9 cm in diameter. Two days after the infestation, an aqueous preparation, at a predetermined concentration, of the active compound (formulated as in Example 5) was sprayed over the leaves at a rate of 20 ml per pot. Then, the pots were put in a greenhouse. 10 days later, the acaricidal effect was evaluated and expressed on the following scale:

3 – 0% survival of the mites
2 — not more than 5% survival
1 — more than 5% survival up to 50% survival
0 — more than 50% survival The results are shown in Table 5.

Table 5

| Compound No. | Control effect at a concentration of active ingredient (ppm) of | | |
|---|---|---|---|
| | 1000 | 300 | 100 |
| (1) | 3 | 3 | 3 |
| (2) | 3 | 3 | 3 |
| (3) | 3 | 3 | 3 |
| (4) | 3 | 3 | 3 |
| (5) | 3 | 3 | 3 |
| (6) | 3 | | |
| (7) | 3 | 3 | |
| (8) | 3 | 3 | |
| (9) | 3 | | |

Table 5-continued

| Compound No. | Control effect at a concentration of active ingredient (ppm) of | | |
|---|---|---|---|
| | 1000 | 300 | 100 |
| (10) | 3 | | |
| (11) | 3 | | |
| (A) | 0 | 0 | 0 |

EXAMPLE 8

Test on the mite Tetranychus cinnabarinus (irrigation test)

The leaves of kidney bean plants in the two-leaf stage were infested with 50 to 100 imagos of Tetranychus cinnabarinus.

Two days later, an aqueous preparation, at a predetermined concentration, of the active compound (formulated as in Example 5) was fed, by irrigation, to the roots of the kidney bean plants at a rate of 20 ml per pot. Then, the pots were placed in a greenhouse, and 10 days later, the acaricidal effect was evaluated and expressed on the following scale:

3 — 0% survival of the mites
2 — not more than 5% survival
1 — more than 5% survival up to 50% survival
0 — more than 50% survival The results are shown in Table 6.

Table 6

| Compound No. | Control effect at a concentration of active ingredient (ppm) of | | |
|---|---|---|---|
| | 1000 | 300 | 100 |
| (1) | 3 | 3 | 3 |
| (2) | 3 | 3 | |
| (3) | 3 | 3 | 3 |
| (4) | 3 | 3 | |
| (5) | 3 | 3 | 3 |
| (6) | 3 | 3 | |
| (9) | 3 | 3 | |
| (10) | 3 | 3 | |
| (A) | 0 | 0 | 0 |

EXAMPLE 9

Test on Meloidogyne incognita acrita

An active-compound preparation was prepared by pulverizing and mixing 2 parts by weight of the active compound and 98 parts by weight of talc.

The active compound processed as above was added to soil infested by Meloidogyne incognita acrita in such amounts as to give a concentration of 50 ppm, 25 ppm, 10 ppm and 5 ppm, respectively. The mixture was stirred and mixed uniformly and then charged into pots each of 0.0002 are. In the treated soil were sown about 20 seeds of tomato (variety: KURIHARA) per pot. The tomato seeds were cultivated in a greenhouse. Four weeks later, the grown roots were withdrawn without damaging them, and the degree of injury of 10 roots out of them was evaluated based on the following ratings to determine a root-knot index:

Degree of Injury

0 — no root-knot formation (perfect control)
1 — slight root-knot formation
3 — much root-knot formation
4 — most root-knot formation (corresponding to non-treatment)

$$\text{Root-knot index} = \frac{\Sigma(\text{rating} \times \text{number of roots})}{\begin{pmatrix}\text{total number of}\\\text{examined roots}\end{pmatrix} \times 4} \times 100$$

From the above, the following control effect was obtained:

$$\text{Control Effect} = \frac{\begin{pmatrix}\text{root-knot index}\\\text{of untreated plot}\end{pmatrix} - \begin{pmatrix}\text{root-knot index}\\\text{of treated plot}\end{pmatrix}}{\text{root-knot index of untreated plot}} \times 100$$

A control effect of 100% means a perfect control. The results are shown in Table 7.

Table 7

| Compound No | Control effect (%) at a concentration of active ingredient (ppm) of | | | |
|---|---|---|---|---|
| | 50 | 25 | 10 | 5 |
| (1) | 100 | 100 | | |
| (2) | 100 | 100 | 100 | |
| (3) | 100 | 100 | 100 | 100 |
| (4) | 100 | 100 | | |
| (6) | 100 | 100 | 100 | |
| (7) | 100 | | | |
| (8) | 100 | 100 | 100 | |
| (9) | 100 | 100 | | |
| (11) | 100 | | | |
| (A) | 0 | 0 | 0 | 0 |

EXAMPLE 10

Test on the irrigation effect against *Piricularia oryzae* (Glass Chamber Test)

Solvent: 3.6 parts by weight of dimethylformamide
Emulsifier: 0.15 part by weight of alkylaryl polyglycol ether
Water: 96.25 parts by weight A concentrated solution was obtained by mixing the amount of the active compound that is required to formulate the test chemical in a predetermined concentration with the solvent and the emulsifier in the above amounts; this solution was then diluted with the above amount of water.

Aquatic rice plants (variety: Asahi) were cultivated in paddy-field soil contained in ceramic pot 0.01 m² in area. Each pot contained 5 plants which were kept in water to a depth of 1 to 2 cm. At the 4 to 5-leaf stage, a 0.08% solution of the active compound formulated in the above-described manner was poured directly onto the water surface with a pipette at a rate of 10 ml per pot in a way that did not allow the solution to contact the rice plants directly. The dosage corresponded to 8 kg of the active compound per hectare.

Four days later, the rice plants were spray-inoculated with a suspension of *Piricularia oryzae* spores in a customary manner. The plants were then left for 24 hours in an inoculation chamber at 23° – 25° C and 100% relative humidity. The pots were then moved to a glass hot chamber at 20° to 28° C. On the 8th day after the inoculation, the number of normal lesions developed on the leaves of the rice plants were counted and compared with the number of lesions that occurred on the leaves of untreated but inoculated rice plants, and the disease preventive ratio (%) was calculated. At the same time the damage attributable to the phytotoxicity of the active compound was also assessed visually. The symbol (—) indicates a complete absence of phytotoxic damage. The results are shown in Table 8.

Table 8

| | Results of the Test on the Irrigation Effect against *Piricularia oryzae* | | |
|---|---|---|---|
| Compound No. | Number of lesions per leaf | Disease Preventive Ratio (%) | Damage |
| (3) | 0 | 100 | — |
| (B) | 3.3 | 84 | — |
| Untreated control | 20.5 | 0 | — |

Other ways of formulating the compounds of the present invention are illustrated by the following examples:

EXAMPLE 11

A wettable powder was prepared by pulverizing and mixing 15 parts of compound No.1, 80 parts of a mixture (1:5) of diatomaceous earth and kaolin, and 5 parts of an emulsifier (a polyoxyethylenealkyl phenyl ether). This could be diluted with water to 0.05% before application by spraying.

EXAMPLE 12

An emulsifiable concentrate was prepared by mixing and stirring 30 parts of compound No.4, 30 parts of xylene, 30 parts of methylnapthalene and 10 parts of a polyoxyethylene alkylphenyl ether. This could be diluted with water to 0.05% before spraying.

EXAMPLE 13

A dusting agent was prepared by pulverizing and mixing 2 parts of compound No.2 and 98 parts of a mixture (1:3) of talc and clay. This could be applied by scattering.

EXAMPLE 14

A dusting agent was prepared by pulverizing and mixing 1.5 parts of compound No.7, 0.5 part of isopropyl hydrogen phosphate (PAP), and 98 parts of a mixture (1:3) of talc and clay.

EXAMPLE 15

10 parts of compound No.10, 10 parts of bentonite, 78 parts of a mixture (1:3) of talc and clay, and 2 parts of lignin sulfonate were mixed. 25 parts of water were added to the mixture. The whole was mixed thoroughly and then processed with an extrusion granulator into granules of 20 to 40 mesh, which were dried at 40°–50° C.

EXAMPLE 16

95 parts of clay powder having a particle size distribution of 0.2 to 2 mm were placed in a rotary mixer. During rotation, there were sprayed over the particles 5 parts of a solution of compound No.11 in an organic solvent, thereby wetting them uniformly. Then, drying at 40 to 50° C was effected in order to form granules.

EXAMPLE 17

An oil preparation was prepared by mixing and stirring 0.5 part of compound No.5, 20 parts of a highboiling aromatic compound and 79.5 parts of kerosine.

It will be appreciated that the instant specification and claims are set forth by way of illustration and not

What is claimed is:

1. An O-alkyl-N-sulfamyl-phosphoramidothiolate of the formula $$\begin{array}{c} R^1O \\ R^2S \end{array} \!\! \overset{R}{\underset{\|}{P}} \!\! - \!\! N \!\! \begin{array}{c} R^3 \\ SO_2N \!\! \begin{array}{c} R^4 \\ R^5 \end{array} \end{array}$$

in which
R$^1$ is alkyl with 1–6 carbon atoms,
R$^2$ is alkyl or alkenyl with up to 6 carbon atoms,
R$^3$ is alkyl with 1–6 carbon atoms or phenyl,
R$^4$ is alkyl with 1–6 carbon atoms,
R$^5$ is alkyl with 1–6 carbon atoms or phenyl, and
X is oxygen or sulfur.

2. A method of combating arthropods, nematodes or fungi, which comprises applying to the arthropods, nematodes or fungi, or to a habitat thereof, an arthropodicidally, nematicidally or fungicidally effective amount of a compound according to claim 1.

3. A compound according to claim 1, in which
R$^1$ is alkyl with 1–4 carbon atoms,
R$^2$ is alkyl with 1–4 carbon atoms or alkenyl with 2–4 carbon atoms,
R$^3$ is alkyl with 1–4 carbon atoms or phenyl,
R$^4$ is alkyl with 1–4 carbon atoms, and
R$^5$ is alkyl with 1–4 carbon atoms or phenyl.

4. A compound according to claim 1 wherein such compound is O-ethyl-S-n-propyl-N-methyl-N-(diethylsulfamyl) phosphoramidothiolate of the formula $$\begin{array}{c} C_2H_5O \\ CH_3CH_2CH_2S \end{array} \!\! \overset{O}{\underset{\|}{P}} \!\! - \!\! N \!\! \begin{array}{c} CH_3 \\ SO_2N \!\! \begin{array}{c} C_2H_5 \\ C_2H_5 \end{array} \end{array}$$

5. A compound according to claim 1 wherein such compound is O-ethyl-S-n-propyl-N-methyl-N-(dimethylsulfamyl) phosphoramidothiolate of the formula $$\begin{array}{c} C_2H_5O \\ CH_3CH_2CH_2S \end{array} \!\! \overset{O}{\underset{\|}{P}} \!\! - \!\! N \!\! \begin{array}{c} CH_3 \\ SO_2N \!\! \begin{array}{c} CH_3 \\ CH_3 \end{array} \end{array}$$

6. A compound according to claim 1 wherein such compound is O-ethyl-S-allyl-N-methyl-(dimethylsulfamyl) phosphoramidothiolate of the formula $$\begin{array}{c} C_2H_5O \\ CH_2\!=\!CHCH_2S \end{array} \!\! \overset{O}{\underset{\|}{P}} \!\! - \!\! N \!\! \begin{array}{c} CH_3 \\ SO_2N \!\! \begin{array}{c} CH_3 \\ CH_3 \end{array} \end{array}$$

7. A compound according to claim 1 wherein such compound is O-ethyl-S-n-propyl-N-methyl-N-(N'-methyl-N'-phenylsulfamyl)-phosphoramidothiolate of the formula $$\begin{array}{c} C_2H_5O \\ CH_3CH_2CH_2S \end{array} \!\! \overset{O}{\underset{\|}{P}} \!\! - \!\! N \!\! \begin{array}{c} CH_3 \\ SO_2N \!\! \begin{array}{c} CH_3 \\ Phenyl \end{array} \end{array}$$

8. A compound according to claim 1 wherein such compound is O-ethyl-S-n-propyl-N-phenyl-N-(dimethylsulfamyl)-phosphoramidothiolate of the formula $$\begin{array}{c} C_2H_5O \\ CH_3CH_2CH_2S \end{array} \!\! \overset{O}{\underset{\|}{P}} \!\! - \!\! N \!\! \begin{array}{c} Phenyl \\ SO_2N \!\! \begin{array}{c} CH_3 \\ CH_3 \end{array} \end{array}$$

9. A compound according to claim 1 wherein such compound is O-ethyl-S-n-propyl-N-methyl-N-(dimethylsulfamyl)-phosphoramidodithioate of the formula $$\begin{array}{c} C_2H_5O \\ CH_3CH_2CH_2S \end{array} \!\! \overset{S}{\underset{\|}{P}} \!\! - \!\! N \!\! \begin{array}{c} CH_3 \\ SO_2N \!\! \begin{array}{c} CH_3 \\ CH_3 \end{array} \end{array}$$

10. An arthropodicidal, nematicidal or fungicidal composition containing as active ingredient an arthropodicidally, nematicidally or fungicidally effective amount of a compound according to claim 1 in admixture with a diluent.

11. The method according to claim 2 in which said compound is
O-ethyl-S-n-propyl-N-methyl-N-(diethylsulfamyl) phosphoramidothiolate,
O-ethyl-S-n-propyl-N-methyl-N-(dimethylsulfamul) phosphoramidothiolate,
O-ethyl-S-allyl-N-methyl-N-(dimethylsulfamyl)-phosphoramidothiolate,
o-ethyl-S-n-propyl-N-methyl-N-(N'methyl-N'-phenylsulfamy) phosphoramidothiolate,
O-ethyl-S-n-propyl-N-methyl-N-(N'phosphoramidothiolate or
O-ethyl-S-n-propyl-N-methyl-N-(dimethylsulfamyl)-phosphoramidodithioate.

* * * * *